US00PP33498P2

(12) United States Plant Patent
Hansen

(10) Patent No.: US PP33,498 P2
(45) Date of Patent: Sep. 21, 2021

(54) ***HIBISCUS* PLANT NAMED 'BLACKBERRY MERLOT'**

(50) Latin Name: ***Hibiscus* hybrid**
Varietal Denomination: Blackberry Merlot

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 17/300,223

(22) Filed: Apr. 16, 2021

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608
See application file for complete search history.

*Primary Examiner* — Anne Marie Grunberg

(57) ABSTRACT

A new and distinct cultivar of winter-hardy, herbaceous, perennial, hybrid *Hibiscus* plant named 'Blackberry Merlot' comprising a compact, upright, mounded habit of multiple, well-branched, basal stems producing flowers beginning in late July for at least eight weeks. Flowers have overlapping, moderately-rippled petals of deep velvety red with dark reddish shiny eye, with the leading margin occasionally folded underneath giving flowers extra strength and resistance to wind damage. The flower buds are dark, purplish gray. The foliage is primarily three-lobed, and rich olive-green with mahogany coloration when young.

2 Drawing Sheets

Botanical classification: *Hibiscus* hybrid (L.).
Variety denomination: 'Blackberry Merlot'.

STATEMENT REGARDING PRIOR DISCLOSURES UNDER 37 CFR 1.77(b)(6)

The first non-enabling disclosures were a brief description and photograph of the new plant on Feb. 1, 2020 on the website operated by Walters Gardens, Inc. and subsequently the "Walters Gardens 2020-2021 Catalog" released on May 20, 2020. The first disclosure, in the form of a sale, was made by Walters Gardens, Inc. on Apr. 20, 2020. Walters Gardens, Inc. obtained the new plant and all information relating thereto, from the inventor. No plants of *Hibiscus* 'Blackberry Merlot' have been sold, in this country or anywhere in the world, by any name, nor has any disclosure of the new plant been made more than one year prior the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'Blackberry Merlot' hybridized under direction of the inventor Aug. 4, 2016 at a wholesale perennial nursery in Zeeland, Mich. The new plant is a self-pollination of the unreleased, proprietary hybrid known as 15-105-1 (not patented). Into the trial process the new plant was assigned the breeder code labeled 16-129-1. The parent has a complex mixture of species in them, comprising the species: *moscheutos* and *coccineus*.

*Hibiscus* 'Blackberry Merlot' was first asexually propagated in late summer of 2018 by sterile shoot-tip tissue culture and later by shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Blackberry Merlot' differs from its parents as well as all other hardy herbaceous *Hibiscus* known to the applicant in many traits. The most similar *Hibiscus* cultivars known to the applicant are: 'Vintage Wine' U.S. Plant Pat. No. 27,839, 'Robert Fleming' U.S. Plant Pat. No. 14,776, 'Heartthrob' U.S. Plant Pat. No. 24,760 and 'Midnight Marvel' U.S. Plant Pat. No. 24,079. 'Vintage Wine' has a taller habit, the foliage is ovate and less mahogany blushed, and the flower color has a more reddish-orange hue. 'Robert Fleming' has a shorter and broader habit with foliage that is ovate and less mahogany blushed and the flower petals are narrower and less imbricate. 'Heartthrob' has a shorter and broader habit, ovate foliage of dark green and the flowers open flatter with petals that are more reddish purple and pollen that is brighter yellow. 'Midnight Marvel' has a more rounded habit, and the flower color is more scarlet.

The parent plant is taller in habit, the foliage lighter green, the flowers lighter shade of red and the petals are less furrowed.

*Hibiscus* 'Blackberry Merlot' is a unique hardy herbaceous *Hibiscus* with the following combined traits:

1. Winter-hardy compact perennial with upright, mounded habit of multiple, well-branched, basal stems;
2. Many rotate flowers opening nearly flat with petals of deep velvety-red with a dark reddish shiny eye;
3. Petals are overlapping and moderately rippled giving extra strength and resistance to wind damage;
4. Flowers produced over a long period from late July for at least eight weeks;
5. Flower buds are dark, purplish-gray buds;
6. Primarily three-lobed foliage of rich olive-green with mahogany color when young.

BRIEF DESCRIPTION OF THE DRAWINGS

The photographs of 'Blackberry Merlot' demonstrate the overall appearance of the plant, including the unique traits. The colors are as accurate as reasonably possible with color reproductions. Ambient light spectrum, source and direction may cause the appearance of minor variation in color. The plants in the photographs are from a three-year-old plant in an outdoor trial garden in Zeeland, Mich.

DETAILED BOTANICAL DESCRIPTION

Figure 1:
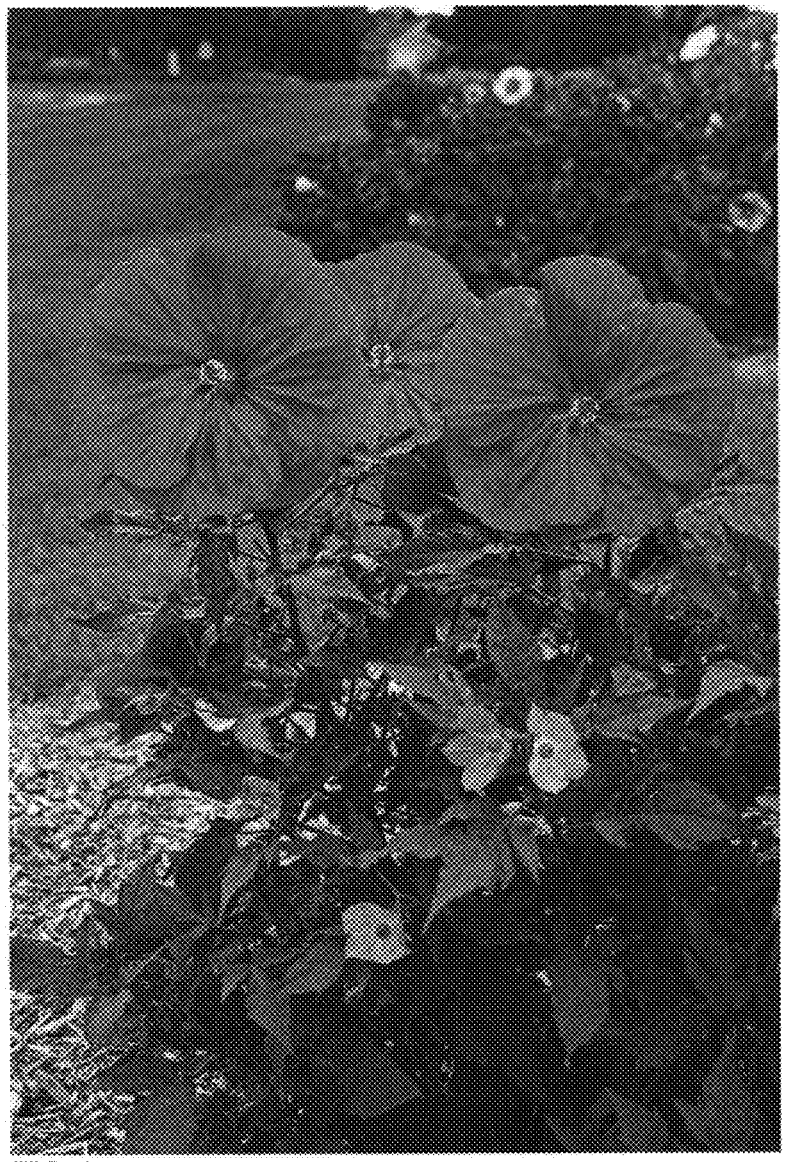
FIG. 1 shows the landscape habit of the new plant in full flower.
Figure 2:
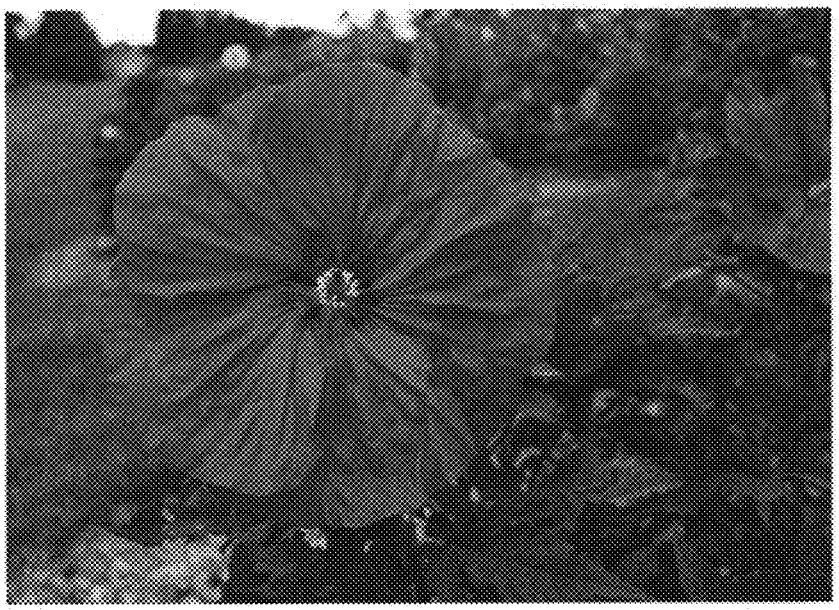
FIG. 2 shows a close-up of the flower.
Figure 3:
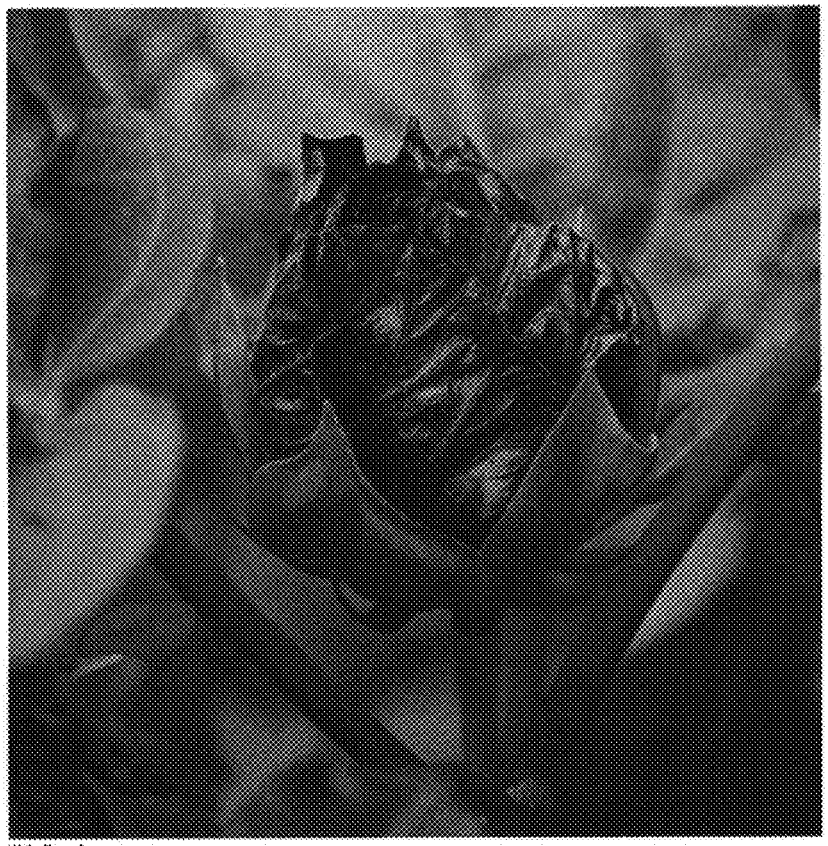
FIG. 3 shows the bud about a day before opening.

The following descriptions and color references are based on the 2015 edition of The Royal Horticultural Society Colour Chart except where common dictionary terms are used. The new plant, *Hibiscus* 'Blackberry Merlot', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-field full-sun garden of a nursery in Zeeland, Mich. with supplemental fertilizer and water as needed. The plants are of natural habit and were not treated with plant growth regulators, nor were they pinched at any time in the growth year.

Parentage: The female or seed parent is the unreleased, non-patented, proprietary *Hibiscus* known by the breeder code 15-105-1, the male or pollen parent is the same plant known by the breeder code 15-105-1;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2.0 cm diameter, fleshy; root color between RHS 158A and RHS 161D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about seven thick, upright, heavily-branched stems producing an upright mound to about 95.0 cm tall and about 120.0 cm wide; flowering from base to top of plant with up to about 20 flowers in the upper main stem in addition to up to 52 flowers on the branches of a single stem.

*Stem*.—Terete, glabrous, glaucous; to about 92.0 cm tall and about 3.2 cm diameter at base, average about 86.0 cm tall and about 2.2 cm diameter at base.

*Stem color*.—Proximal main stems between RHS 137B and RHS 138A with lenticular marks of nearest RHS 145C; distal main stems variable with portions receiving high light nearest RHS 183A and portions shaded nearest RHS 146D.

*Lateral branches*.—To 14 per stem, average about 8 per stem; terete; glabrous; glaucous; to about 47.0 cm long and 1.5 cm diameter at base, smaller distally.

*Lateral branch color*.—Proximally between RHS 137B and RHS 138A with lenticular marks of nearest RHS 145C; distal main stems variable with portions receiving high light nearest RHS 183A and portions shaded nearest RHS 146D.

*Internode*.—Branches beginning at lowest node and about 16 below single flowers; average about 30 nodes per stem; internode length about 3.0 cm of unpinched plant.

*Internode color*.—Same as surrounding stem.

Foliage description: Typically tri-lobed, rarely up to penta-lobed; alternate; coarsely and irregularly serrate; apex and side lobes narrowly acute; base truncate to cordate; micro-puberulent abaxial and adaxial; moderately to deeply incised, to about 20.0 mm from petiole; adaxial and abaxial surfaces dull; leaf blades to about 19.0 cm long and about 15.0 cm across, average blade size 15.0 cm long and 12.0 cm wide; center lobe largest, to about 10.0 cm long and 3.2 cm across; no fragrance detected;

*Foliage color*.—Young expanding leaves — adaxial variable nearest RHS 138A with strong blush to solid portion between RHS 187A and RHS N187A, abaxial nearest RHS 146B with moderate to random blushing of nearest RHS 187A; mature late season leaves — adaxial between RHS 139A and RHS NN137A, abaxial nearest RHS 147A.

*Veins*.—Palmate; dull adaxial and abaxial; slightly applanate adaxial, costate on abaxial.

*Vein color*.—Young adaxial nearest RHS 187C, abaxial between RHS 187B and RHS 187C; mature adaxial midrib proximally nearest RHS 145C and distal midrib nearest RHS 146C, secondary veins nearest RHS 146C; abaxial midrib and proximal veins nearest RHS 145C and distal midrib and secondary veins nearest RHS 146B.

*Petioles*.—Applanate adaxial to abaxial, asperous adaxial and abaxial; glabrous; to about 8.5 cm long and 5.0 mm diameter at base, average about 6.5 cm long and 4.0 mm wide at base.

*Petiole color*.—Lower leaves adaxial and abaxial between RHS 138B and RHS 147C, distal leaves between RHS 183C and RHS 187C.

Flower description: Complete; perfect; actinomophic; rotate; mostly outward facing; to about 22.0 cm across and 8.5 cm deep, decreasing distally; petals opening flat to slightly recurved distally; with a lustrous dark reddish center eye about 5.5 cm across;

*Buds one day prior to opening flat*.—Globose with acute apex and truncate base; sepals proximally adpressed to petals and distally flaring; to about 4.6 cm long and about 3.8 cm diameter in middle.

*Bud color one day prior to anthesis*.—Exposed petal color nearest RHS N187A and calyx nearest RHS 138A moderately blushed with RHS N186C.

*Epicalyx*.—Typically 12 per flower; linear; margin ciliolate; glabrous; dull surface abaxial and adaxial; narrowly acute apex and truncate base, arcuate upwards near apex; about 25.0 mm long and about 3.5 mm wide at base.

*Epicalyx color*.—Adaxial distally nearest RHS 146C, and proximally nearest RHS 146B; abaxial between RHS 144A and RHS 38A and moderately blushed with nearest RHS 187A.

*Calyx*.—Broadly campanulate, forming star-shaped hypanthium; to about 1.0 cm deep and 7.0 cm across at apices.

*Sepals*.—Five; ovate; acute apex; fused in basal 15.0 mm; margin entire, edentate; micro-puberulent and matte adaxial and abaxial; about 3.5 cm long, about 2.5 cm wide at just distal to fusion.

*Sepal color*.—Adaxial distally nearest RHS 146C and proximally nearest RHS 146B, with veins of nearest RHS 145C; abaxial between RHS 144A and RHS 138A moderately blushed with nearest RHS 187A and without obvious veins.

*Inflorescence*.—Solitary, up to 72 per branched stem without pinching; nearly flat face; mostly outwardly facing.

*Flower lastingness*.—Persist for one to two days; effective for at least 8 weeks beginning late July.

*Flower fragrance*.—No detectable fragrance.

*Petals*.—Five; micro-puberulent adaxial and abaxial; adaxial eye zone lustrous, remaining distal adaxial portion and entire abaxial matte; adnate to the androecium to form a column, leading edge (inside) occasionally folded under between to 3.0 mm; imbricate to about 100% overlapping at widest part (petals overlapping 100% to the petals on either side); slightly bullate; undulation moderate; palmately veined, primary veins slightly furrowed on adaxial and slightly costate abaxial; apex rounded with distinct basal claw and limb; margins entire, edentate.

*Petal size*.—Average about 15.0 cm across and about 10.3 cm long, claw base about 8.0 mm across (smaller in later part of flowering season); dark reddish eye extending about 2.0 cm from base with melded transition to the deep velvety reddish distal portion.

*Petal color*.—Adaxial proximal 2.0 cm portion near column nearest a RHS 187B, the distal portion nearest RHS 59A with a slight undertone of nearest RHS 187B; abaxial nearest RHS 59A except basal 10 mm of claw between RHS 59C and RH 59D.

*Gynoecium*.—Single; partially enclosed in column; Staminal column: glabrous and lustrous; about 4.2 cm long and about 11.0 mm across at base; with pistil exserted about 29.0 mm above top of column; Column color: between RHS 59C and RHS 61C; Style: cylindrical; exserted above column 29 mm, pentafurcate in distal 12 mm; to 67 mm long, 1.0 mm diameter at base and 2.0 mm diameter below split; micro-puberulent in region above staminal column, glabrous within column; color in column base nearest RHS 155A, middle portion nearest RHS NN155A and exposed distal portion more purple than RHS 53A, split portion between RHS 59A and RHS 187B; Stigma: typically five; globose, puberulent, about 4.0 mm in diameter and 1.0 mm tall; color RHS 187B; Ovary: superior; globose, longitudinally grooved; rounded to broadly acute apex and flat truncate base; about 5.0 mm across at base and about 6.0 mm tall; acute apex; color nearest RHS 146D.

*Androecium*.—Numerous, approximately 125 to 150; Filaments: terete; lustrous and glabrous; slightly arcuate toward stigma; adnate entire column; variable length, about 3.0 to 6.0 mm long and about 0.3 mm diameter; color nearest RHS 59B; Anthers: irregular globose; dorsifixed; longitudinal; about 2.7 mm long and 1.5 mm across and about 1.0 mm thick; variable color between RHS 31D and irregularly blushed nearest RHS 51B; Pollen: abundant, globose, less than 0.1 mm long; color between RHS 20C and RHS 161C.

Pedicel: Cylindrical; glabrous; glaucous; average size from base of sepal to abscission point about 1.8 cm long and 4.0 mm diameter, from abscission point to stem node about 2.0 cm long and about 3.5 mm wide; longer on early flowers and decreasing in distal flowers; upwardly;

Pedicel color: Nearest RHS 146D lightly blushed with nearest RHS 187A distal and proximal abscission point;

Peduncle: Cylindrical; glabrous: glaucous; to about 92.0 cm tall and about 3.2 cm diameter at base, average about 86.0 cm tall and about 2.2 cm diameter at base;

Peduncle color: Proximal main stems between RHS 137B and RHS 138A with lenticular marks of nearest RHS 145C; distal main stems variable with portions receiving high light nearest RHS 183A and portions shaded nearest RHS 146D;

Fruit and seed: Not yet observed, but not tested for sterility;

Resistance: *Hibiscus* 'Blackberry Merlot' has not displayed any pest and disease susceptibility or resistance beyond that typical of hardy perennial *Hibiscus*.

Culture: The plant grows best with plenty of moisture.

Hardiness at least from USDA zone 4 through 9.

I claim:

1. A new cultivar of hardy herbaceous perennial *Hibiscus* hybrid plant named 'Blackberry Merlot' as herein illustrated and described.

* * * * *